(12) United States Patent
Osypka et al.

(10) Patent No.: US 7,187,980 B2
(45) Date of Patent: Mar. 6, 2007

(54) CARDIAC LEAD WITH STEROID ELUTING RING

(75) Inventors: Thomas P. Osypka, Palm Harbor, FL (US); Ronald van den Nieuwenhof, Odessa, FL (US)

(73) Assignee: Oscor Inc., Palm Harbor, FL (US)

( * ) Notice: Subject to any disclaimer, the term of this patent is extended or adjusted under 35 U.S.C. 154(b) by 537 days.

(21) Appl. No.: 10/282,203

(22) Filed: Oct. 28, 2002

(65) Prior Publication Data

US 2003/0093136 A1  May 15, 2003

Related U.S. Application Data

(60) Provisional application No. 60/344,984, filed on Nov. 9, 2001.

(51) Int. Cl.
*A61N 1/00* (2006.01)
(52) U.S. Cl. .................................................. 607/120
(58) Field of Classification Search .............. 607/120, 607/126–128, 122
See application file for complete search history.

(56) References Cited

U.S. PATENT DOCUMENTS

| | | |
|---|---|---|
| 3,545,439 A | 12/1970 | Duncan |
| 3,572,344 A | 3/1971 | Bolduc |
| 3,788,329 A | 1/1974 | Friedman |
| 3,804,098 A | 4/1974 | Friedman |
| 3,857,934 A | 12/1974 | Bernstein et al. |
| 4,018,220 A | 4/1977 | Emmett |
| 4,156,429 A | 5/1979 | Amundson |
| 4,191,741 A | 3/1980 | Hudson et al. |
| 4,220,153 A | 9/1980 | Dresback |
| 4,328,812 A | 5/1982 | Ufford et al. |
| 4,352,360 A | 10/1982 | King |
| 4,506,680 A | 3/1985 | Stokes |
| 4,538,623 A | 9/1985 | Proctor et al. |
| 4,577,642 A | 3/1986 | Stokes |
| 4,581,028 A | 4/1986 | Fox, Jr. et al. |
| 4,592,372 A | 6/1986 | Beranek |
| 4,596,576 A | 6/1986 | de Nijs |
| 4,601,893 A | 7/1986 | Cardinal |

(Continued)

FOREIGN PATENT DOCUMENTS

EP  0 819 445 A1  1/1998

(Continued)

OTHER PUBLICATIONS

Please see International Search Report dated Jun. 26, 2003.

(Continued)

*Primary Examiner*—George Manuel
(74) *Attorney, Agent, or Firm*—Scott D. Wofsy; Edwards Angell Palmer & Dodge LLP

(57) ABSTRACT

A cardiac lead is disclosed which includes an elongated lead body having opposed proximal and distal ends, a tip electrode operatively associated with the distal end of the elongated lead body, a connector operatively associated with the proximal end of the elongated lead body and electrically connected to the tip electrode, and a cylindrical eluting ring disposed proximate the tip electrode and formed from a compound including an elastomer and about 15% to 25% by weight medicament.

27 Claims, 6 Drawing Sheets

U.S. PATENT DOCUMENTS

| | | |
|---|---|---|
| 4,606,118 A | 8/1986 | Cannon et al. |
| 4,711,251 A | 12/1987 | Stokes |
| 4,784,161 A | 11/1988 | Skalsky et al. |
| 4,819,661 A | 4/1989 | Heil, Jr. et al. |
| 4,819,662 A | 4/1989 | Heil, Jr. et al. |
| 4,844,099 A | 7/1989 | Skalsky et al. |
| 4,876,109 A | 10/1989 | Mayer et al. |
| 4,953,564 A | 9/1990 | Berthelsen |
| 4,961,931 A | 10/1990 | Wong |
| 4,972,848 A | 11/1990 | Di Domenico et al. |
| 5,002,067 A | 3/1991 | Berthelsen et al. |
| 5,003,992 A | 4/1991 | Holleman et al. |
| 5,217,028 A | 6/1993 | Dutcher et al. |
| 5,232,444 A | 8/1993 | Just et al. |
| 5,255,693 A | 10/1993 | Dutcher et al. |
| 5,269,770 A | 12/1993 | Conway et al. |
| 5,282,844 A | 2/1994 | Stokes et al. |
| 5,324,325 A | 6/1994 | Moaddeb |
| 5,354,327 A | 10/1994 | Smits |
| 5,408,744 A | 4/1995 | Gates |
| 5,447,533 A | 9/1995 | Vachon et al. |
| 5,489,294 A | 2/1996 | McVenes et al. |
| 5,496,360 A | 3/1996 | Hoffmann et al. |
| 5,522,874 A | 6/1996 | Gates |
| 5,531,780 A | 7/1996 | Vachon |
| 5,578,068 A | 11/1996 | Laske et al. |
| 5,776,178 A | 7/1998 | Pohndorf et al. |
| 5,833,715 A * | 11/1998 | Vachon et al. ............... 607/120 |
| 5,844,017 A | 12/1998 | Jamiolkowski et al. |
| 5,893,884 A | 4/1999 | Tu |
| 5,902,330 A * | 5/1999 | Ollivier et al. ............. 607/122 |
| 5,987,746 A | 11/1999 | Williams |
| 5,989,581 A | 11/1999 | Groenewegen |
| 6,038,482 A | 3/2000 | Vachon |
| 6,086,582 A | 7/2000 | Altman et al. |
| 6,102,887 A | 8/2000 | Altman |
| 6,119,042 A * | 9/2000 | Verness et al. ............. 607/122 |
| 6,134,463 A | 10/2000 | Wittkampf et al. |
| 6,141,593 A | 10/2000 | Patag |
| 6,181,972 B1 | 1/2001 | Guedeney et al. |
| 6,198,973 B1 | 3/2001 | Doan et al. |
| 6,249,709 B1 * | 6/2001 | Conger et al. ............. 607/122 |
| 6,278,897 B1 * | 8/2001 | Rutten et al. ............... 607/122 |
| 6,298,272 B1 | 10/2001 | Peterfeso et al. |
| 6,361,780 B1 * | 3/2002 | Ley et al. ................... 424/400 |
| 6,363,286 B1 | 3/2002 | Zhu et al. |
| 6,405,091 B1 * | 6/2002 | Vachon et al. ............. 607/120 |

FOREIGN PATENT DOCUMENTS

| | | |
|---|---|---|
| EP | 0 916 363 A2 | 5/1999 |
| FR | 2 751 232 A1 | 5/1999 |
| WO | WO 91/19533 | 12/1991 |
| WO | WO 95/03083 | 2/1995 |
| WO | WO 96/08286 | 3/1996 |
| WO | WO 00/30610 | 6/2000 |

OTHER PUBLICATIONS

*Pricing and Clinical Electrophysiology*, CARDIOSTIM '94 Proceedings, Edited by Rodolphe Ruffy and Jacques Mugica, Future Publising Comapny, Inc., Armonk, New York, Nov. 1994, vol. 17, No. 11, Part II, pp. 1837-2227.

* cited by examiner

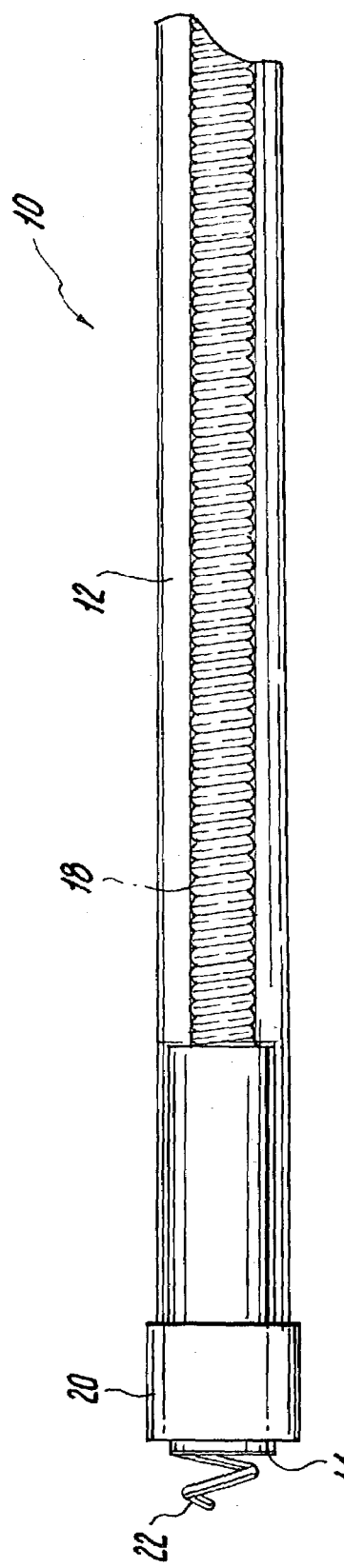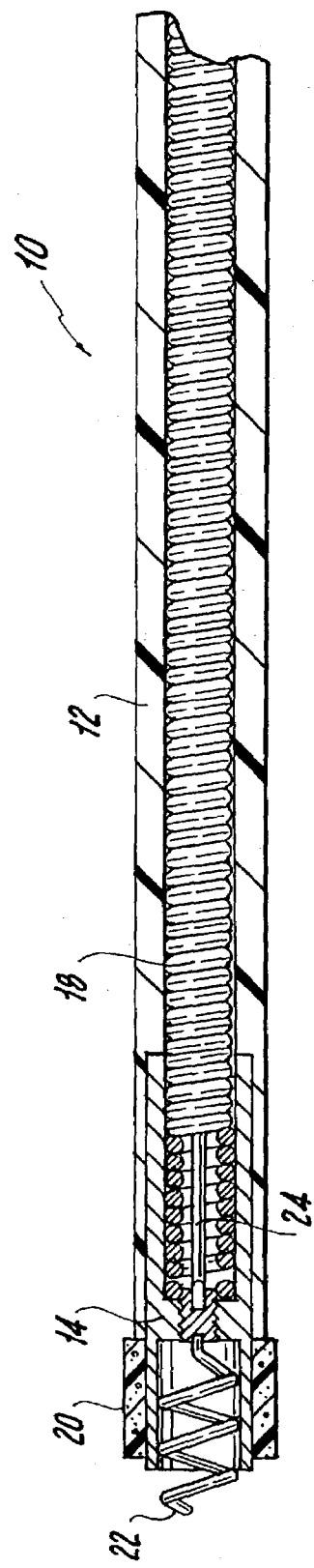

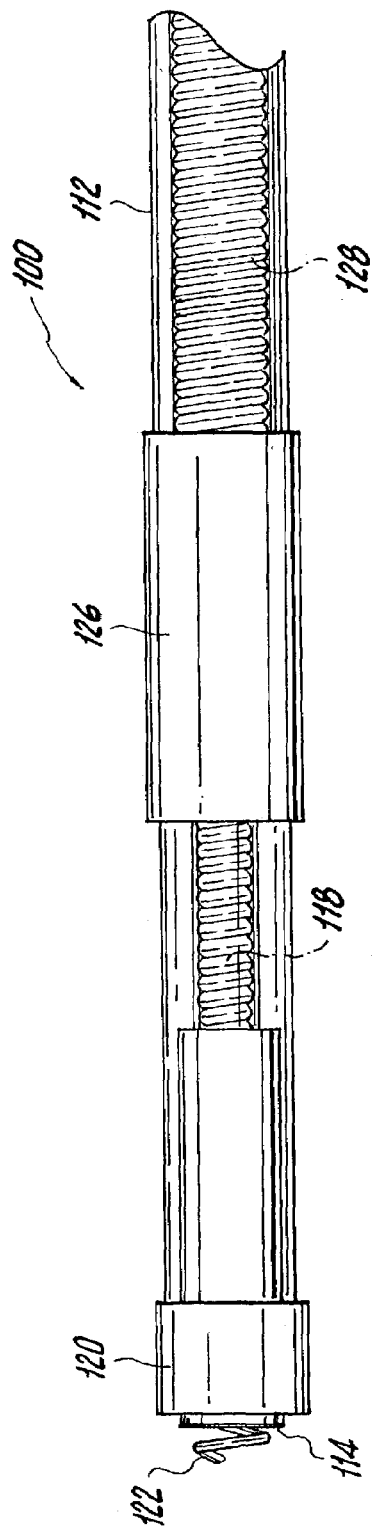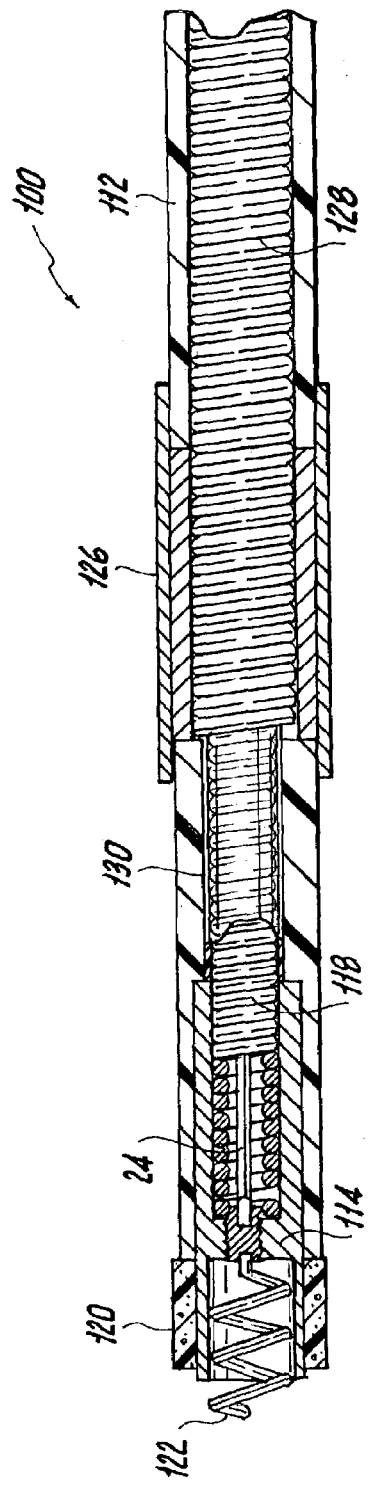

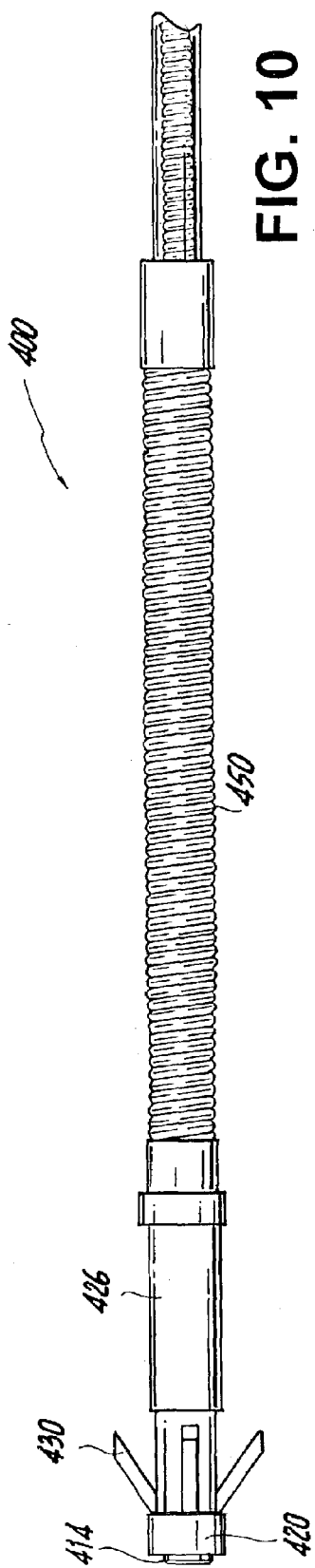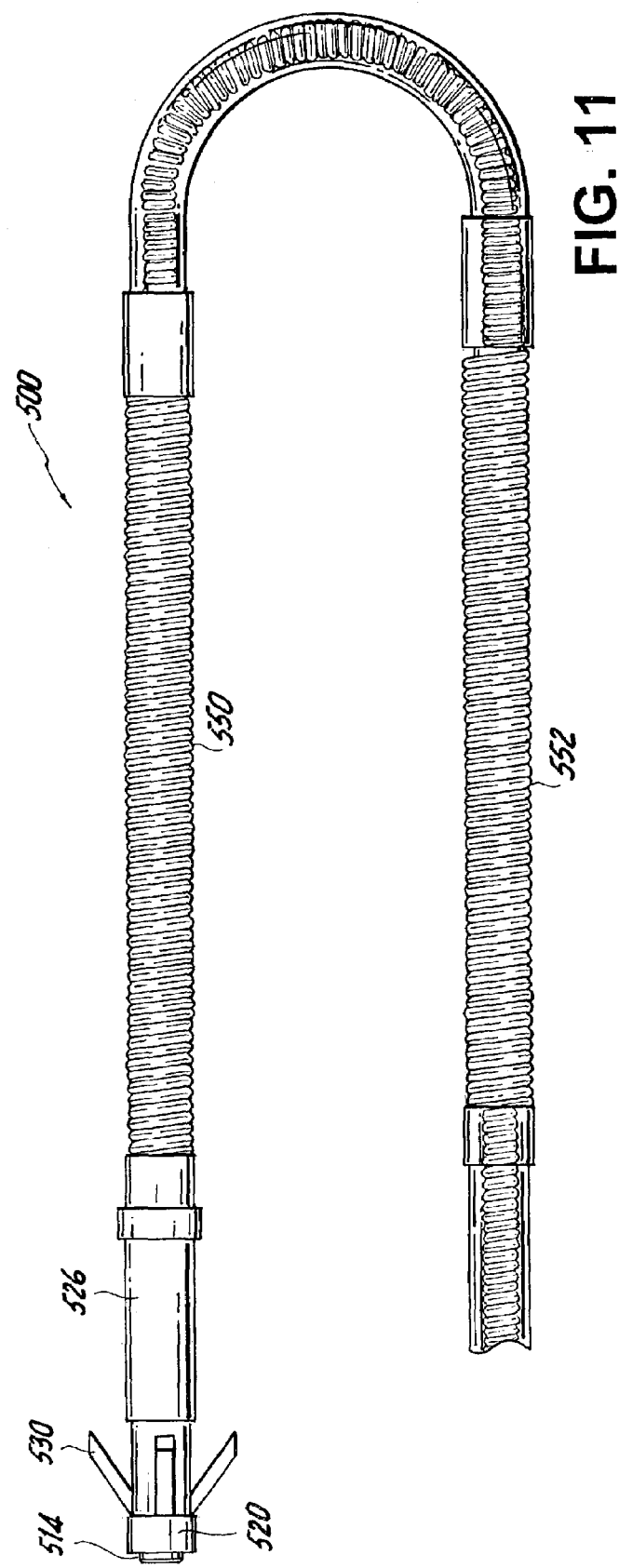

CARDIAC LEAD WITH STEROID ELUTING RING

CROSS-REFERENCE TO RELATED APPLICATIONS

The subject application claims the benefit of priority to U.S. Provisional Patent Application Ser. No. 60/344,984 filed Nov. 9, 2001, the disclosure of which is herein incorporated by reference in its entirety.

BACKGROUND OF THE INVENTION

1. Field of the Invention

The subject invention is directed to cardiac leads, and more particularly, to passive and active unipolar, bipolar, tripolar and quadrupolar endocardial stimulation leads that are adapted and configured to elute a steroid to treat cardiac tissue.

2. Background of the Related Art

Implantable cardiac stimulation leads, including endocardial leads, are well known in the art. In general, these devices have an elongated flexible body with an electrode at one end for contacting cardiac tissue and a connector at the other end for mating with an automated stimulation device, namely a pacemaker or defibrillator. The electrode of an endocardial lead may be secured within a chamber of the heart by passive fixation through the use of a plurality of flexible tines which project outwardly from the end of the lead body, or by active fixation through the use of a helical fixation screw.

When an endocardial lead has been implanted in the heart, either by active or passive fixation, it has been determined that the cardiac tissue at the site of implantation will react favorably to the lead in the presence of a therapeutic drug, such as, for example, a steroid. Consequently, cardiac leads have been designed with means for delivering a therapeutic drug to the cardiac tissue at the implantation site.

One such example of a lead having drug delivery means is disclosed in U.S. Pat. No. 5,902,330 to Ollivier et al. which describes a pacing lead having a frusto-conical diffusion ring fixed in place by gluing. The diffusion ring is constructed of porous silicone and loaded with an active material, such as a steroid, for distributing the steroid in the region of the myocardium adjacent the electrode. Another example of a drug delivery device is disclosed in U.S. Pat. No. 6,361,780 to Ley et al. which describes a microporous bio-compatible collar or annulus having a therapeutic drug within its pores. The collar or annulus is preferably formed from a ceramic material and is designed to surround a portion of a lead or catheter.

SUMMARY OF THE INVENTION

The subject invention is directed to a new and useful cardiac lead that includes an elongated flexible lead body having opposed proximal and distal ends. A tip electrode is operatively associated with the distal end of the elongated lead body, and a connector is operatively associated with the proximal end of the elongated lead body. The connector is electrically connected to the tip electrode by a conductor coil that extends through the interior of the lead body.

A cylindrical eluting ring or collar surrounds the distal tip electrode. The eluting ring is formed from a compound that includes an elastomer and about 15% to 25% by weight medicament. The elastomer is preferably silicone and the medicament is preferably a steroid, and more preferably, either dexamethasone sodium phosphate or dexamethasone sodium acetate. Other steroids may also be employed.

In one embodiment of the subject invention, the lead is adapted for active fixation and includes a retractable fixation screw operatively associated with a distal end portion of the lead body. In another embodiment of the subject invention, the lead is adapted for passive fixation and includes a plurality of flexible tines associated with a distal end portion of the lead body. In yet another embodiment of the subject invention, the lead is adapted for bipolar stimulation and includes a ring electrode spaced from the tip electrode and electrically associated with the connector. In other embodiments of the subject invention, the lead is adapted for defibrillation as well as pacing/sensing. In such instances, the lead may be tripolar or quadrupolar, and may be adapted for passive or active fixation.

These and other aspects of the cardiac lead of the subject invention will become more readily apparent to those having ordinary skill in the art from the following detailed description of the invention taken in conjunction with the drawings described hereinbelow.

BREIF DESCRIPTION OF THE DRAWINGS

So that those having ordinary skill in the art to which the subject invention pertains will more readily understand how to make and use the cardiac leads of the subject invention, embodiments thereof will be described in detail hereinbelow with reference to the drawings, wherein:

FIG. 2 is a side elevational view of the distal portion of the unipolar active fixation lead of FIG. 1;

FIG. 3 is a cross-sectional view of the distal portion of the steroid eluting unipolar active fixation lead of FIG. 1;

FIG. 4 is a side elevational view of the distal portion of a steroid eluting bipolar active fixation lead constructed in accordance with a preferred embodiment of the subject invention;

FIG. 5 is a cross-sectional view of the distal portion of the steroid eluting bipolar active fixation lead of FIG. 4;

FIG. 10 is a side elevational view of the distal portion of a steroid eluting tripolar passive fixation lead constructed in accordance with a preferred embodiment of the subject invention; and FIG. 11 is a side elevational view of the distal portion of a steroid eluting quadrupolar passive fixation lead constructed in accordance with a preferred embodiment of the subject invention.

DETAILED DESCRIPTION OF THE PREFERRED EMBODIMENTS

Figure 1:
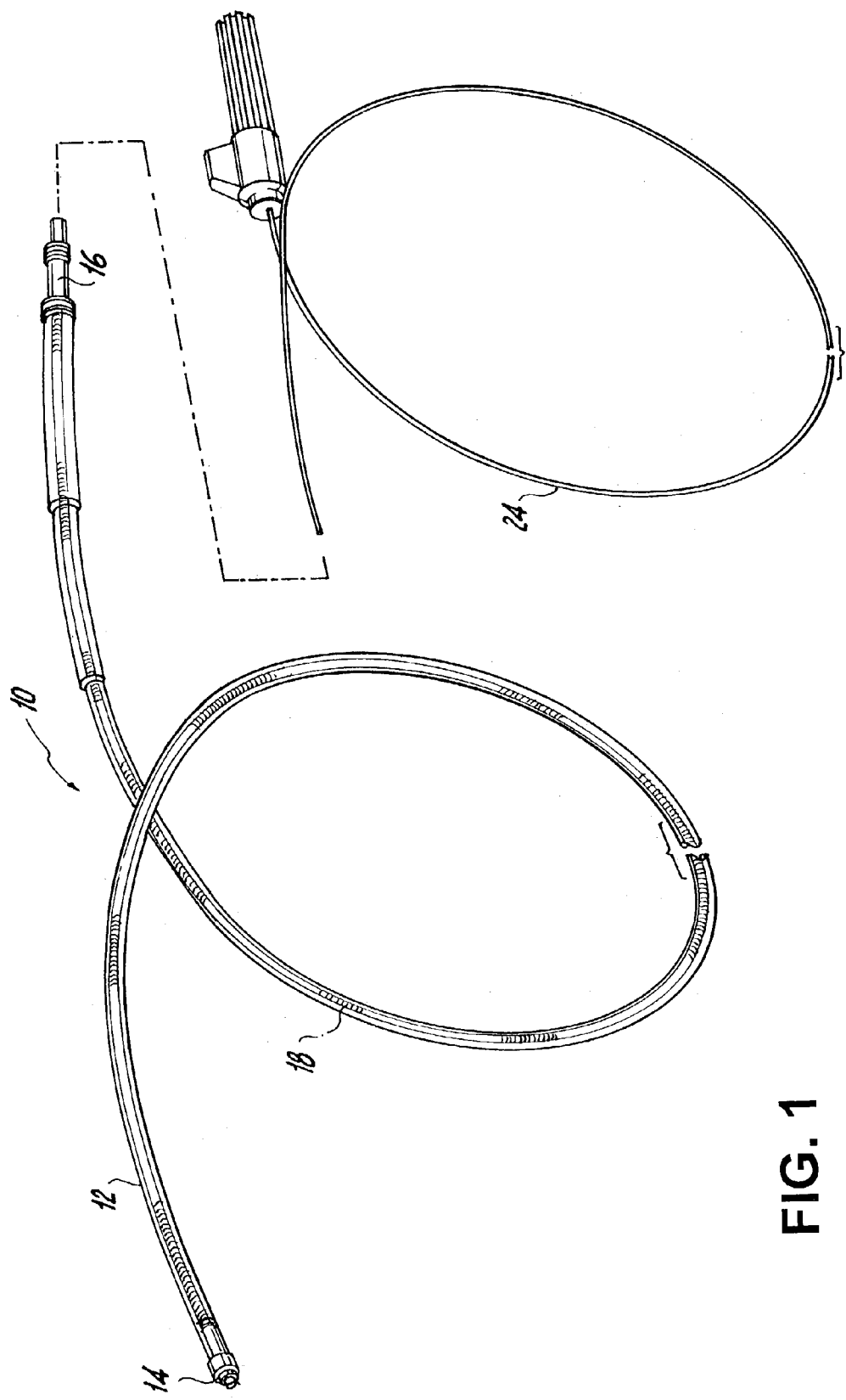
FIG. 1 is a perspective view of a steroid eluting unipolar active fixation lead constructed in accordance with a preferred embodiment of the subject invention.

Referring now to the drawings wherein like reference numerals identify similar aspects of the cardiac leads of the subject invention, there is illustrated in FIG. 1 a unipolar active fixation lead constructed in accordance with a preferred embodiment the subject invention and designated generally by reference numeral 10. Cardiac lead 10 includes an elongated flexible lead body 12 having opposed proximal and distal ends. The lead body 12 is formed from a biocompatible insulative material such as silicone rubber, polyurethane or the like.

With continuing reference to FIG. 1, a tip electrode 14 with an annular contact surface is operatively associated with the distal end of the elongated lead body 12. The tip electrode 14 is coated with or formed from platinum, stainless steel MP35N, a platinum-iridium alloy or a similar material. A connector 16 is operatively associated with the proximal end of the elongated lead body 12. The connector 16 may be of any standard type, size or configuration such as, for example, an IS-1 type connector (International Standard ISO 5841.3:1992). This type of connector may be employed for both unipolar and bipolar pacing/sensing.

Connector 16 is electrically connected to the tip electrode 14 by way of a conductor coil 18 that extends through the interior lumen of lead body 12. The tip electrode 14 has an exposed distal end surface for contacting tissue and a proximal reception bore for receiving conductor coil 18. Conductor coil 18 is generally helical in configuration and includes one or more conductive wires or filaments. For example, the conductor may be a multifilar conductor coil with as many as eight (8) filaments. Other conductors may be employed such as flexible low-ohm DFT drawn filled rope tubing.

As best seen in FIGS. 2 and 3, a cylindrical ring or collar 20 is disposed at the distal end of lead body 12 proximate to or surrounding at least a portion of tip electrode 14. Ring 20 is a therapeutic drug eluting structure that is formed from a compound that includes an elastomer, such as silicone and about 15% to 25% by weight medicament. Preferably, the medicament is a steroid. However, other therapeutic drugs or agents may be employed. In use, the steroid elutes from the elastomer over time having a desirable effect on surrounding cardiac tissue. Suitable steroids include dexamethasone sodium phosphate and dexamethasone sodium acetate. Other steroids may also be used.

Preferably, eluting ring 20 has an axial length of about 1 to 2 mm, and a durometer of about 65 to 90 Shore A. Those skilled in the art will readily appreciate that the geometry and dimensions of the ring may be modified to control the rate at which the steroid is eluted from the silicone. Eluting ring 20 is formed by mixing liquid silicone rubber (LSR) together with the steroid. The composition is then extruded into a tubular form and subsequently cut into rings having a desired length. Alternatively, the composition may be used to mold rings of a desired length. In either instance, after formation, the ring is then glued in place using a silicone adhesive.

The following table sets forth the calculated weight (considering tolerances in tubing diameter and density measurements) of dexamethasone sodium phosphate per ring (based on a ring length of 1.1±0.1 mm) from three different lots of rings formed from a compound containing 19.41% by weight dexamethasone sodium phosphate and 80.59% by weight silicone.

| Lot No. | Inner Diameter (in.) | Outer Diameter (in.) | Weight of Steroid (mg.) |
|---|---|---|---|
| A | .062 ± 0.002 | .095 ± 0.002 | 0.50–0.91 |
| B | .051 ± 0.002 | .088 ± 0.002 | 0.60–0.89 |
| C | .043 ± 0.002 | .075 ± 0.002 | 0.43–0.66 |

With continuing reference to FIG. 2, cardiac lead 10 includes a fixation screw 22 which is operatively associated with the distal end of lead body 12 for actively securing the lead tip to the myocardium during implantation. Fixation screw 22 is defined by a wire helix may be manipulated through use of the screw driver stylet 24 primarily illustrated in FIG. 1, the distal end of which is shown in FIG. 3. The fixation screw may be electrically active to assist in pacing/sensing. Other retraction/extension mechanism are also envisioned. For example, the fixation screw could be retracted/extended by turning one helical coil relative to another coil.

Referring now to FIGS. 4 and 5, there is illustrated another cardiac lead constructed in accordance with a preferred embodiment of the subject invention and designated generally by reference numeral 100. Cardiac lead 100 is substantially identical to cardiac lead 10 in that it has an active fixation screw 122 and a silicone eluting ring 120 containing about 15% to 25% by weight steroid. Cardiac lead 100 differs however from cardiac lead 10 in that it is adapted for bipolar pacing/sensing rather than unipolar pacing. More particularly, cardiac lead 100 includes both a distal tip electrode 114 which defines a cathodic pole and a ring electrode 126 spaced proximally from tip electrode 114 and defining an anodic pole.

As best seen in FIG. 5, an inner conductor coil 118 is operatively associated with the distal tip electrode 114 for delivering energy to the tip electrode from the connector at the proximal end of the elongated flexible lead body 112. The distal tip electrode 114 has an exposed distal end surface for contacting tissue and a proximal reception bore for receiving the inner conductor coil 118. Similarly, an outer conductor coil 128 is operatively associated with the ring electrode 126 for delivering energy to the ring electrode from the connector at the proximal end of the lead body 112. A sheath 130 or similar structure provides a layer of insulation between the inner and outer conductor coils. Alternative wiring arrangements are also envisioned, including multifilar coils in which one or more wires of the coil are connected to each electrode and are separated from one another by an insulating material.

Figure 6:
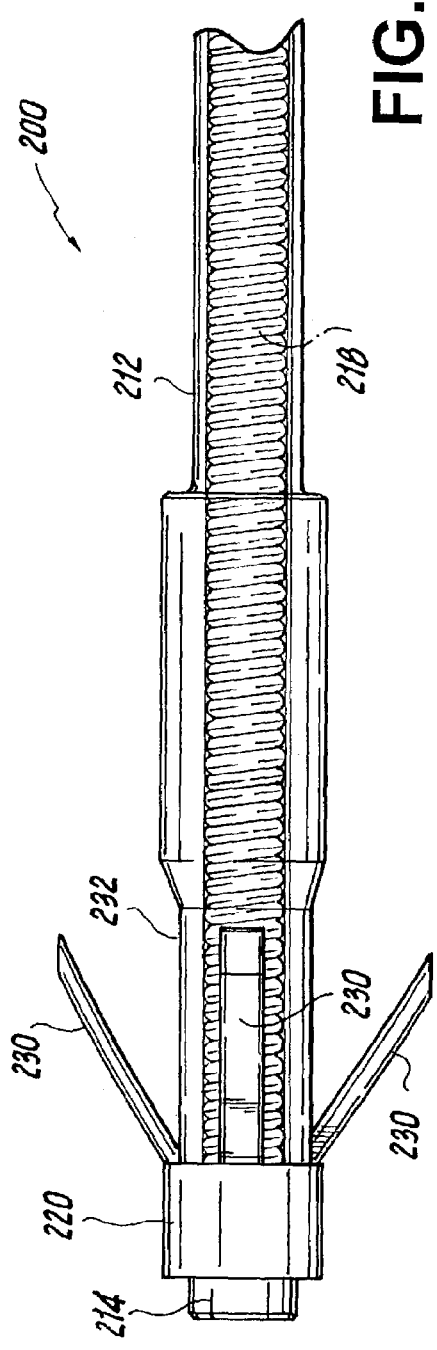
FIG. 6 is a side elevational view of the distal portion of a steroid eluting unipolar passive fixation lead constructed in accordance with a preferred embodiment of the subject invention.
Figure 7:
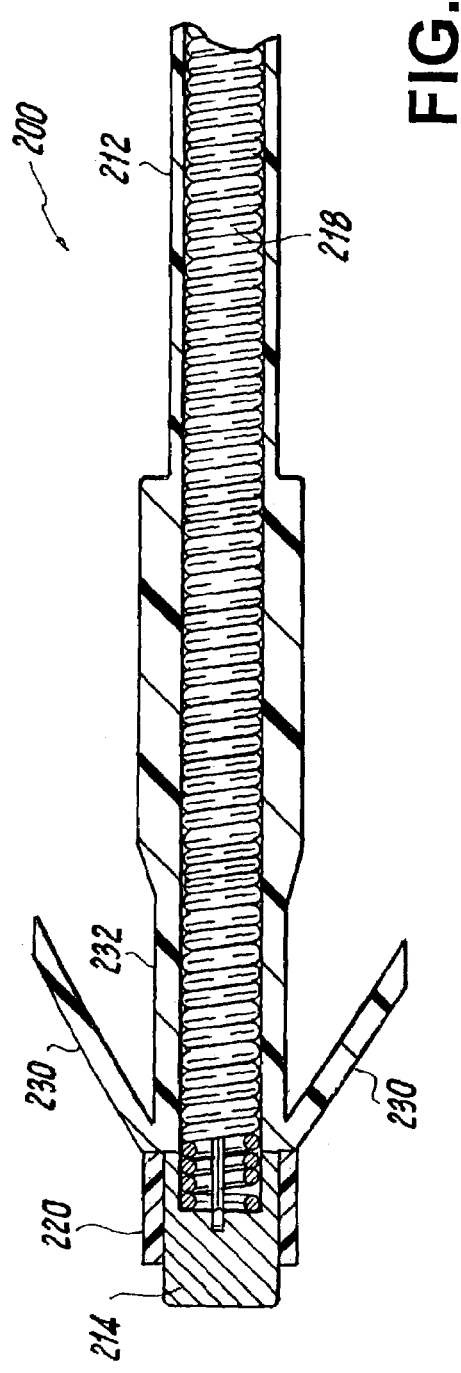
FIG. 7 is a cross-sectional view of the distal portion of the steroid eluting unipolar passive fixation lead of FIG. 6.

Referring to FIGS. 6 and 7, there is illustrated another cardiac lead constructed in accordance with a preferred embodiment of the subject invention and designated generally by reference numeral 200. Cardiac lead 200 is substantially identical to cardiac lead 10 in that it includes a distal tip electrode 214 receiving energy from a coiled conductor 218 and surrounded by a silicone eluting ring 220 containing about 15% to 25% by weight steroid. Cardiac lead 200 differs however from cardiac lead 10 in that cardiac lead 200 is adapted for passive fixation rather than active fixation. More particularly, cardiac lead 200 includes a plurality of outwardly projecting flexible tines 230 rather than a helical fixation screw.

The flexible tines 230 of cardiac lead 200 are formed from silicone rubber and are adapted to keep the lead tip securely anchored within the trabeculae of the heart, and more particularly, within the right ventricle. It is also envisioned that the distal portion of the lead can have a preformed J-shaped configuration so that it may be employed in the right atrium. During implantation, when cardiac lead 200 is introduced into the myocardium within the lumen of a catheter or introducer sheath, the flexible tines 230 deflect into an axially extended position within a circumferential recessed area 232 formed in the distal portion of lead body 212. As a result, the profile of the lead body is substantially uniform.

Figure 8:
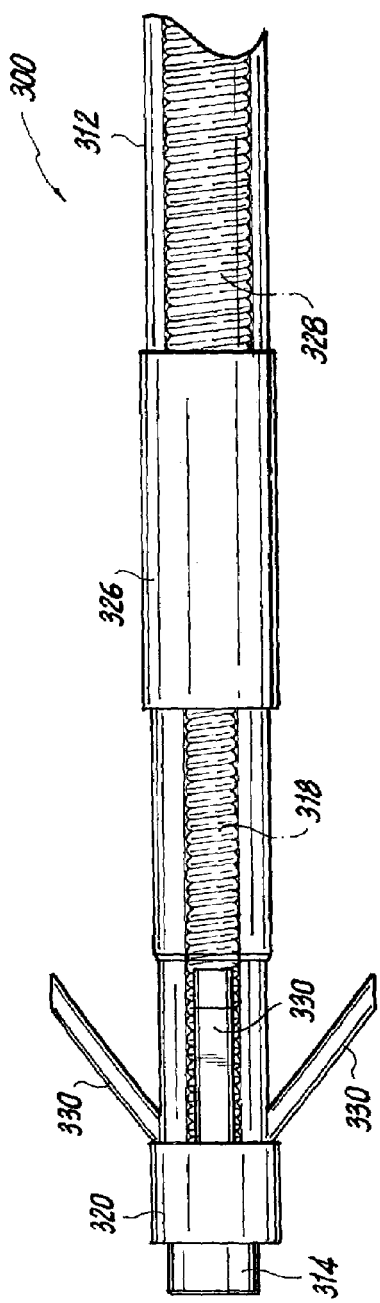
FIG. 8 is a side elevational view of the distal portion of a steroid eluting bipolar passive fixation lead constructed in accordance with a preferred embodiment of the subject invention.
Figure 9:
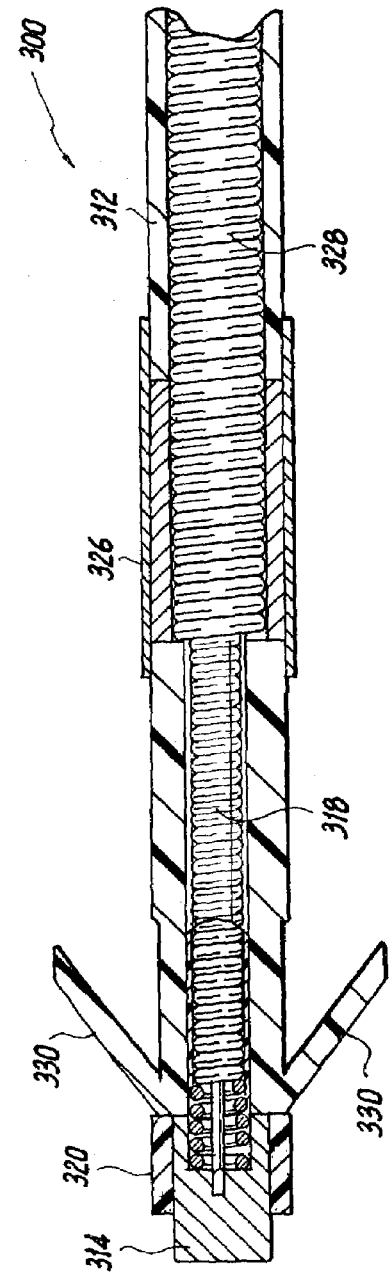
FIG. 9 is a cross-sectional view of the distal portion of the steroid eluting bipolar passive fixation lead of FIG. 8.

Referring to FIGS. 8 and 9, there is illustrated another cardiac lead constructed in accordance with a preferred embodiment of the subject invention and designated generally by reference numeral 300. Cardiac lead 300 is substantially identical to cardiac lead 200 in that it has a plurality of outwardly projecting flexible tines 330 adapted to facilitate passive fixation of the lead tip, and a silicone eluting ring 320 containing about 15% to 25% by weight steroid. Cardiac lead 300 differs however from cardiac lead 200 in that it is adapted for bipolar pacing/sensing rather than unipolar pacing. Thus, cardiac lead 300 includes a cathodic distal tip electrode 314 located at the distal end of lead body 312 and an anodic proximal ring electrode 326 spaced from the distal tip electrode 314. An inner conductor coil 318 is operatively associated with the distal tip electrode 314, and an outer conductor coil 328 is operatively associated with the proximal ring electrode 326.

Referring now to FIG. 10, there is illustrated another cardiac lead constructed in accordance with a preferred embodiment of the subject invention and designated generally by reference numeral 400. Cardiac lead 400 is a tripolar lead in that it includes a cathodic distal tip electrode 414 and an anodic proximal ring electrode 426 which are used for pacing/sensing, and a shocking coil 450 that is used for right ventricular defibrillation. In this tripolar configuration, shocking coil 450 serves as a ground. Like each of the other embodiment disclosed herein, cardiac lead 400 includes a silicone eluting ring 420 containing about 15% to 25% by weight steroid. As illustrated, lead 400 has outwardly projecting flexible tines 430 adapted to facilitate passive fixation, but the lead can include an active fixation screw as illustrated for example in FIG. 2. While not shown, the proximal portion of lead 400 is preferably bifurcated and includes a bipolar IS-1 type connector associated with electrodes 414 and 426, and a unipolar DF-1 type connector (International Standard ISO 11318:1993) associated with shocking coil 450.

Referring to FIG. 11, there is illustrated yet another cardiac lead constructed in accordance with a preferred embodiment of the subject invention and designated generally by reference numeral 500. Cardiac lead 500 is a quadrupolar lead in that it includes a cathodic distal tip electrode 514 and an anodic proximal ring electrode 526 which are used for pacing/sensing, and two shocking coils 550 and 552 that are used for defibrillation. More particularly, the distal shocking coil 550 is used for right ventricular stimulation while the proximal shocking coil 552 is used to stimulate the superior vena cava. In certain circumstances, cardiac lead 500 may be employed in such a manner so that the distal shocking coil 550 serves normally as a pacing/sensing anode, but during defibrillation it serves as a shocking coil.

Cardiac lead 500 includes a silicone eluting ring 520 containing about 15% to 25% by weight steroid. The lead is shown with outwardly projecting flexible tines 530, but an active fixation screw may be employed. The proximal portion of lead 500 is preferably trifurcated in that it includes a bipolar IS-1 type connector associated with electrodes 514 and 526, a first unipolar DF-1 type connector associated with distal shocking coil 550, and a second unipolar DF-1 type connector associated with proximal shocking coil 552.

Although the subject invention have been described with respect to preferred embodiments, those skilled in the art will readily appreciate that changes and modifications may be made thereto without departing from the spirit and scope of the subject invention as defined by the appended claims.

What is claimed is:

1. A cardiac lead comprising:
 a) an elongated lead body having opposed proximal and distal ends;
 b) a tip electrode operatively associated with the distal end of the elongated lead body and having an exposed distal end surface and a proximal reception bore;
 c) a connector operatively associated with the proximal end of the elongated lead body and electrically connected to the tip electrode by a conductor coil received within the proximal reception bore of the tip electrode; and
 d) a cylindrical eluting ring disposed at the distal end of the lead body proximate to the exposed distal end surface of the tip electrode, having an axial length of about 1 mm to 2 mm, surrounding the tip electrode and formed from a compound including silicone and about 15% to 25% by weight medicament, the eluting ring being dimensioned and configured in such a manner so as to control the rate at which the medicament is eluted from the silicone, and wherein the cylindrical eluting ring has: (i) an exposed outer diametrical eluting surface; and (ii) an exposed distal annular eluting surface in close proximity to the exposed distal end surface of the tip electrode for treating surrounding cardiac tissue over time, and wherein the axial distance between the exposed distal annular eluting surface of the eluting ring and the exposed distal end surface of the tip electrode is substantially less than the axial length of the eluting ring.

2. A cardiac lead as recited in claim 1, wherein the lead is adapted for active fixation and includes a retractable fixation screw operatively associated with a distal end portion of the lead body.

3. A cardiac lead as recited in claim 1, wherein the lead is adapted for passive fixation and includes a plurality of flexible tines associated with a distal end portion of the lead body.

4. A cardiac lead as recited in claim 1, wherein the lead is adapted for bipolar stimulation and includes a ring electrode spaced proximally from the tip electrode and electrically connected to the connector.

5. A cardiac lead as recited in claim 1, wherein the compound from which the eluting ring is formed includes about 15% to 25% by weight steroid.

6. A cardiac lead as recited in claim 1, wherein the compound from which the eluting ring is formed includes about 15% to 25% by weight dexamethasone sodium phosphate.

7. A cardiac lead as recited in claim 1, wherein the compound from which the eluting ring is formed includes about 15% to 25% by weight dexamethasone sodium acetate.

8. A cardiac lead as recited in claim 1, wherein the eluting ring has a durometer of about 65 to 90 Shore A.

9. A cardiac lead as recited in claim 1, wherein the conductor comprises a conductor coil which extends through the lead body for electrically connecting the tip electrode to the connector.

10. A cardiac lead configured for active fixation comprising:
   a) an elongated lead body having opposed proximal and distal ends;
   b) an annular tip electrode operatively associated with the distal end of the elongated lead body and having an exposed distal end surface and a proximal reception bore;
   c) a retractable fixation screw operatively associated with a distal portion of the lead body;
   d) a connector operatively associated with the proximal end of the elongated lead body and electrically connected to the tip electrode by a conductor coil received within the proximal reception bore of the tip electrode; and
   e) a cylindrical eluting ring disposed at the distal end of the lead body proximate to the exposed distal end surface of the tip electrode, having an axial length of about 1 mm to 2 mm, surrounding the tip electrode and formed from a compound including silicone and about 15% to 25% by weight medicament, the eluting ring being dimensioned and configured in such a manner so as to control the rate at which the medicament is eluted from the silicone, and wherein the cylindrical eluting ring has: (i) an exposed outer diametrical eluting surface; and (ii) an exposed distal annular eluting surface in close proximity to the exposed distal end surface of the tip electrode, for treating surrounding cardiac tissue over time, and wherein the axial distance between the exposed distal annular eluting surface of the eluting ring and the exposed distal end surface of the tip electrode is substantially less than the axial length of the eluting ring.

11. A cardiac lead as recited in claim 10, wherein the lead is adapted for bipolar stimulation and includes a ring electrode spaced from the tip electrode and electrically connected to the connector.

12. A cardiac lead as recited in claim 11, wherein the conductor comprises at least one multifilar conductor coil extending through the lead body for electrically connecting the tip electrode and the ring electrode to the connector.

13. A cardiac lead as recited in claim 10, wherein the compound from which the eluting ring is formed includes about 15% to 25% by weight dexamethasone sodium phosphate.

14. A cardiac lead as recited in claim 10, wherein the compound from which the eluting ring is formed includes about 15% to 25% by weight dexamethasone sodium acetate.

15. A cardiac lead as recited in claim 10, wherein the eluting ring has a durometer of about 65 to 90 Shore A.

16. A cardiac lead as recited in claim 10, wherein the conductor comprises a conductor coil which extends through the lead body for electrically connecting the tip electrode and the connector.

17. A cardiac lead configured for bipolar stimulation comprising:
   a) an elongated lead body having opposed proximal and distal ends;
   b) a cathodic tip electrode operatively associated with the distal end of the elongated lead body and having an exposed distal end surface and a proximal reception bore;
   c) an anodic ring electrode spaced proximally from the tip electrode;
   d) a connector operatively associated with the proximal end of the elongated lead body and electrically connected to the tip electrode by a conductor coil received within the proximal reception bore of the tip electrode and electrically connected to the ring electrode; and
   e) a cylindrical eluting ring disposed at the distal end of the lead body, having an axial length of about 1 mm to 2 mm, disposed proximate to the exposed distal end surface of the tip electrode and formed from a compound including silicone and about 15% to 25% by weight medicament, the eluting ring being dimensioned and configured in such a manner so as to control the rate at which the medicament is eluted from the silicone, and wherein the cylindrical eluting ring has: (i) an exposed outer diametrical eluting surface; and (ii) an exposed distal annular eluting surface in close proximity to the exposed distal end surface of the tip electrode, for treating surrounding cardiac tissue over time, and wherein the axial distance between the exposed distal annular eluting surface of the eluting ring and the exposed distal end surface of the tip electrode is substantially less than the axial length of the eluting ring.

18. A cardiac lead as recited in claim 17, wherein the lead is adapted for active fixation and includes a retractable fixation screw operatively associated with a distal end portion of the lead body.

19. A cardiac lead as recited in claim 17, wherein the lead is adapted for passive fixation and includes a plurality of flexible tines associated with a distal end portion of the lead body.

20. A cardiac lead as recited in claim 17, wherein the compound from which the eluting ring is formed includes about 15% to 25% by weight dexamethasone sodium phosphate.

21. A cardiac lead as recited in claim 17, wherein the compound from which the eluting ring is formed includes about 15% to 25% by weight dexamethasone sodium acetate.

22. A cardiac lead as recited in claim 17, wherein the eluting ring has a durometer of about 65 to 90 Shore A.

23. A cardiac lead as recited in claim 17, wherein the connector is an IS-1 type connector.

24. A cardiac lead as recited in claim 17, wherein the conductor comprises at least one multifilar conductor coil extending through the lead body for electrically connecting the tip electrode and the ring electrode to the connector.

25. A cardiac lead as recited in claim 17, further comprising at least one defibrillation coil spaced proximally from the ring electrode.

26. A cardiac lead as recited in claim 25, further comprising at least one additional connector operatively associated with the proximal end of the elongated lead body and electrically connected to the at least one defibrillation coil.

27. A cardiac lead as recited in claim 26, wherein the connector is a DF-1 type connector.

* * * * *